United States Patent [19]

Falke

[11] Patent Number: 4,597,899
[45] Date of Patent: Jul. 1, 1986

[54] PROCESS FOR OBTAINING A FACTOR XIII PREPARATION, AND ITS USE

[75] Inventor: Jürgen Falke, Marburg, Fed. Rep. of Germany

[73] Assignee: Behringwerke Aktiengesellschaft, Marburg, Fed. Rep. of Germany

[21] Appl. No.: 737,058

[22] Filed: May 23, 1985

[30] Foreign Application Priority Data

May 25, 1984 [DE] Fed. Rep. of Germany ....... 3419581

[51] Int. Cl.$^4$ ........................... C07K 3/20; C07K 3/22; C07K 3/24; A61K 35/48
[52] U.S. Cl. .................................. 530/383; 424/101; 424/105; 514/2; 514/8; 514/21; 530/851; 530/416
[58] Field of Search ................... 260/112 B; 424/101, 424/105; 514/2, 8, 21

[56] References Cited

U.S. PATENT DOCUMENTS

| | | | |
|---|---|---|---|
| 3,310,471 | 3/1967 | Parcells | 424/105 |
| 3,409,605 | 11/1968 | Florini | 260/112 R |
| 3,904,751 | 9/1975 | Zwisler et al. | 424/105 |
| 3,931,399 | 1/1976 | Bohn et al. | 424/105 |
| 4,285,933 | 8/1981 | Fukushima et al. | 424/105 |
| 4,327,086 | 4/1982 | Fukushima et al. | 424/105 X |

Primary Examiner—Howard E. Schain
Attorney, Agent, or Firm—Finnegan, Henderson, Farabow, Garrett & Dunner

[57] ABSTRACT

A process for obtaining a factor XIII preparation is described, in which the factor XIII is precipitated from a placental extract using an alcohol, and is adsorbed onto an anion exchanger, and the exchanger is washed and the factor XIII is eluted. The factor XIII preparation obtained can be used for the treatment of disturbances of blood coagulation.

4 Claims, No Drawings

PROCESS FOR OBTAINING A FACTOR XIII PREPARATION, AND ITS USE

The invention relates to a process for obtaining a factor XIII preparation from placenta. This preparation can be used for the treatment of disturbances of blood coagulation.

Processes for the preparation of a medicament having a fibrin-stabilizing action, which means the same as containing factor XIII, have already been described in German Pat. Nos. 2,063,069 and 2,063,070. In these two multi-stage processes, factor XIII is precipitated using diaminoethoxyacridine lactate. It is costly to use this precipitant. Another process, which is likewise multi-stage, is disclosed in European Pat. No. 0,011,739, in which, in one process step, factor XIII is precipitated using an alkylene oxide polymer.

It has now been found, surprisingly, that a factor XIII preparation can be obtained from placentae in higher yields than by processes of the state of the art, starting from an ethanol precipitation of a salt extract from placentae, and adsorption of the dissolved precipitate on DEAE-cellulose, substantial removal of impurities by washing of the exchanger, and elution of the factor XIII.

Thus, the invention relates to a process for obtaining a factor XIII preparation from an aqueous extract from placentae, which comprises precipitating the factor XIII with a lower alkanol, dissolving the residue in an aqueous solution, bringing the solution into contact with an anion exchanger, removing the liquid, washing the exchanger with a liquid which does not desorb factor XIII, and eluting the factor XIII.

Ethanol is preferably used for the alkanol precipitation, the concentration of the alcohol being adjusted to 100–300 ml/l, preferably 150–300. The pH is 7–9, preferably 7.5–7.7. The temperature is maintained between 0° and −10° C., preferably −5° and −7° C.

The residue is dissolved in an aqueous liquid at a conductivity of less than 10 mS and a pH of 5–9, and the solution is filtered where appropriate and brought into contact with an anion exchanger, preferably DEAE-cellulose, the amount of moist exchanger paste being 100–500, preferably 200–300, ml/l of liquid. It is possible to mix the liquid and the ion exchanger, the contact time being 0.5–5, preferably 1, hour, or the liquid can be passed through a column containing the exchanger. The pH should be between 7 and 9.

The liquid and the ion exchanger are separated, and the ion exchanger is washed with an aqueous liquid at a conductivity of up to 3, preferably 1–2, mS and at a pH of 7–9, preferably 7.5–7.7, preferably until the washing liquid is free of protein.

The exchanger is treated with an aqueous liquid which has a conductivity above 2 mS, preferably with a salt solution which contains a complexing agent, preferably with a solution containing at least 5 g of sodium chloride per l of water, by which means the factor XIII is desorbed, and the solution is, where appropriate, concentrated or brought to dryness.

The yield is up to 50% of the activity contained in the placentae.

Albumin can be obtained from the supernatant from the alkanol precipitation, and immunoglobulins can be obtained from the solution which has been treated with anion exchanger and from the washing liquids of the ion exchanger.

The factor XIII preparation obtained can, if appropriate after further measures, be used for the treatment of disturbances of blood coagulation.

EXAMPLE 5 mmol of EDTA were added to 10.3 l of an extract obtained by treatment of comminuted placental material with the same amount by weight of an aqueous solution containing 5 g of sodium chloride per liter, and ethanol was added to the mixture at pH 7.6 and −6° C. until it contained 250 ml of ethanol per l. It was stirred for 1 hour, 50 g/l Celite J 2 filtration aid (prewashed with 5 mmol/l EDTA solution) were added, and the mixture was filtered. The residue was suspended 3 times in 1.6 l of a solution containing tris and EDTA, each 5 mmol/l, and the mixture was stirred and filtered. The combined eluates were concentrated in an ultrafilter to 1,590 ml which contained 10,600 U of factor XIII.

The concentrate, which had a conductivity of 2 mS, was stirred with 375 g of moist DEAE-cellulose for 2 hours. The protein solution was filtered off with suction, and the filter cake was washed with 1,350 ml of a buffer containing tris and EDTA, each 5 mmol per l.

For the desorption, the DEAE-cellulose was stirred for 45 minutes in 1,600 ml of an aqueous solution of pH 7.2, containing 8.5 g of NaCl and 5 mmol of EDTA per l. After filtration of the solution, this procedure was repeated twice. The eluates were combined. They contained 8,302 U of factor XIII activity. Before further processing, this protein solution can be concentrated in an ultrafilter or freeze-dried.

I claim:

1. A process for obtaining a factor XIII preparation from an aqueous extract of placentae, which comprises precipitating the factor XIII for said extract with a lower alkanol, dissolving the residue in an aqueous solution, bringing the solution into contact with an anion exchanger, removing the liquid, washing the exchanger with a liquid which does not desorb factor XIII, and eluting the factor XIII.

2. The process as claimed in claim 1, wherein the alkanol is ethanol, and the concentration of the alcohol in the mixture is 150–300 ml/l.

3. The process as claimed in claim 1, wherein the anion exchanger is DEAE-cellulose.

4. The process as claimed in claim 1, wherein the ion exchanger is washed with an aqueous liquid having a conductivity of 1–2 mS.

* * * * *